US006417349B1

(12) United States Patent
Kim et al.

(10) Patent No.: US 6,417,349 B1
(45) Date of Patent: *Jul. 9, 2002

(54) **WATER-SOLUBLE EXTRACT OF ASIATICOSIDE AND MADECASSOSIDE FROM *CENTELLA ASIATICA* AND ISOLATING METHOD THEREOF**

(76) Inventors: Kweon Kim, Rm. 1203, Jugong Apt. No. 908, 257 Myong il-dong, Kangdong-ku, Seoul; Seung-Yong Lee, Rm. 1105, Greentown Apt. No. 103, Bup-Dong, Daeduk-ku, Daejun City; Sung-Ki Seo, Rm. 302, Hangun Villa A-dong, 102 Gyosung-li, Jinchun-eup, Jinchun-kun, Chung Buk; Byeong-Ryong Hwang, Rm. 504, Jugong Apt. No. 905, 257 Myong il-dong, Kangdong-ku; Jin-Kyu Park, Rm. 206, Hanyang Apt. No. 4, 54 Myong il-dong, Kangdong-ku, both of Seoul, all of (KR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/957,958

(22) Filed: Oct. 27, 1997

(30) Foreign Application Priority Data

Mar. 24, 1997 (KR) ............................................. 97-10114

(51) Int. Cl.$^7$ ................................................. C07H 1/00
(52) U.S. Cl. ........................... 536/128; 536/127; 514/26
(58) Field of Search ............................. 514/26; 536/127, 536/128

(56) References Cited

U.S. PATENT DOCUMENTS 5,166,139 A * 11/1992 Bombardelli et al. ......... 574/26

FOREIGN PATENT DOCUMENTS

| KR | 87-1458 | 8/1987 |
| KR | 87-1573 | 9/1987 |
| KR | 91-2518 | 4/1991 |

OTHER PUBLICATIONS

Poizot et al., C.R. Acad. Sci. [D], 286, 1978, pp. 789–792.

P.K. Inamdar et al., "Determination of Biologically Active Constituents in *Centella Asiatica*", (1996) Journal of Chromatography A. 742, pp. 127–130.

B. Diallo et al., "Direct Coupling of High–Speed Counter–Current Chromatography to Thin–Layer Chromatography Application to the Separation of Asiaticoside and Madecassoside from *Centella Asiatica*," (1991) Journal of Chromatography, 558 pp, 446–450.

* cited by examiner

*Primary Examiner*—Elli Peselev
(74) *Attorney, Agent, or Firm*—Hickman Stephens Coleman & Hughes, LLP

(57) ABSTRACT

A water-soluble extract of asiaticoside and madecassoside from *Centella asiatica* and an isolating method thereof. In the isolating method an aqueous alcohol containing *Centella asiatica* is subjected to cold-precipitation to obtain an extract. The extract in the aqueous alcohol is treated with a halogenide solvent for layer separation, and then the aqueous layer is extracted with a higher alcohol. The extract in the alcohol layer is washed first with sodium hydroxide and then with water. After being concentrated, the extract is crystallized with ethyl acetate to obtain crystals and the crystals are washed. A method for treating liver cells in a mammal includes administering to a mammal an effective amount of the extract from *Centella asiatica* containing asiaticoside and madecassoside.

2 Claims, No Drawings

WATER-SOLUBLE EXTRACT OF ASIATICOSIDE AND MADECASSOSIDE FROM *CENTELLA ASIATICA* AND ISOLATING METHOD THEREOF

BACKGROUND OF THE INVENTION

1. Field of the Invention

The present invention relates to a water-soluble extract of asiaticoside and madecassoside from *Centella asiatica*, which is able to protect liver cells with an anti-fibrosis effect, and to an isolating method thereof.

2. Description of the Prior Art

*Centella asiatica* (L.) Urb, a family of umbelliferea which is autogenous in Madagascar island of Africa and India, has been used for the treatment of a local wound since a long time ago (Poizot. A., Dumez. D, C.R. Acad. Sci [D] 286, 1978). Many researchers report that the titrated extract of *Centella asiatica* (hereinafter referred to as "TECA") is effective to a local injury of the tissues. In fact, TECA is acknowledged as a medicinal effector and commercially available under the tradename of "Madecassol" (asiaticoside:asiatic acid:madecassic acid=4:3:3). Its medicinal effect is to restore a damaged tissue to a nearly original state by modifying the fibrosis progress with protection of the cells in the tissue.

These components, however, are limited to the curing of surgical wounds and their extraction, as disclosed in Korean Pat. Publication Nos. 87-1458, 87-1573 and 91-2518, requires elaborate processes, so that the yield and purity thereof is poor. In addition, the objective main components are genin (asiatic acid, madecassic acid and madasiatic acid) and asiaticoside, which are both water-insoluble so that there is a limit in expanding their uses.

SUMMARY OF THE INVENTION

Although the pre-existing TECA exhibits an excellent effect of anti-fibrosis, its physical property of water insolubility forces itself to be in the form of powder, limiting its application range to the curing of surgical wound.

Intensive research repeated by the present inventors aiming to expand the pharmaceutical use of TECA, resulted in the finding that a treatment of *Centella asiatica* with an aqueous alcohol greatly helps extract the components which are soluble in water and effective in the protection and the anti- fibrosis of liver cells.

Therefore, it is an object of the present invention to provide a water-soluble extract of asiaticoside and madecassoside from *Centella asiatica*, which shows an excellent effect of the protection and the anti-fibrosis of liver cells.

It is another object of the present invention to provide an isolating method of the water-soluble extract.

In accordance with an aspect of the present invention, there is provided a method for isolating a water-soluble extract of asiaticoside and madecassoside from *Centella asiatica*, comprising the steps of: subjecting an aqueous alcohol containing *Centella asiatica* to cold-precipitation; treating the extract in the aqueous alcohol with a halogenide solvent for layer separation; extracting the aqueous layer with a higher alcohol; washing the extract in the alcohol layer with sodium hydroxide, then with water and concentrating the extract; crystallizing the extract with ethyl acetate, to give a crystal; and washing the crystal.

In accordance with another aspect of the present invention, there is provided a water-soluble extract of asiaticoside and madecassoside from *Centella asiatica*, which is able to protect liver cells with an anti-fibrosis effect.

DETAILED DESCRIPTION OF THE INVENTION

1. Isolation of the Extract of Asiaticoside and Madecassoside

*Centella asiatica* is immersed in an alcohol solution in water, to give an extract solution which is, then, treated with a halogenide solvent. The aqueous layer was extracted with an alcohol ($C_n>4$). Subsequently, the extract in the alcohol layer was washed several times with an aqueous alkaline solution, and concentrated in vacuo or subjected to precipitation, to give a solid.

Showing a solubility in water, this solid mainly comprises asiaticoside and madecassoside.

The alcohol solution used in the present invention comprises a methanol or ethanol with an alcohol content ranging 50–80%. The halogenide solvent useful in the present invention is selected from the group consisting of methylene chloride, chloroform, dichloroethane, and dichloroethene. For the extraction from the aqueous layer, an alcohol containing at least 4 carbon atoms, such as that selected from the group consisting of normal butanol, sec-butanol and amyl alcohol, is used. As the alkaline solution, and aqueous sodium hydroxide or potassium hydroxide solution is employed.

The extract from *Centella asiatica* obtained by the above procedure consist mainly of asiaticoside and madecassoside with a ratio ranging from 4:6 to 6:4, and it is found that the two components constitute 97% or more of the extract. It can be dissolved in water, alcohol and vegetable oil. Particularly, because the solubility of the extract in water is a very important physical property, it is called water soluble TECA (hereinafter referred to as "WS-TECA") in the present invention.

2. Test for the Protection of Liver Cells

After carbon tetrachloride ($CC_4$), known as a representative toxic material, and galactosamine were used to induce a toxicity in the primarily cultured liver cells of wistars, WS-TECA was tested for the effect of toxicity interception and restoration.

A) Test animal

Wistars (male, 150–200 g) were allowed to eat feed and water as much as they like at a temperature of $22\pm1°$ C. and at a humidity of $60\pm5\%$ while day and night were changed every 12 hours. They were starved for one day before the test.

B) Culture of the liver cell of the wistars

The liver cells were isolated by a two-stage collagenase perfusion technique, a little modified Berry-Friend method. The wistar was put under anesthesia with urethane (1 g/1 kg weight body) and its abdomen was cleaned with 70% ethanol and cut open. The portal fissue vein was intubated with a 20 gauge catheter through which 150 ml of HBBS was allowed to flow at a rate of 15 ml/min. In this while, its inferior vena cava was cut to remove the blood. After its thorax was open and a 18 gauge catheter was inserted into the inferior vena cava, it was corded for the re-circulation of a digestive juice comprising 0.05% collagenase in 95 ml of HBBS. The re-circulation was carried out for 10 min while supplying a mix of $CO_2$ (5%) and $O_2$ (95%). When liver cells were separated, the liver was picked out and placed in 60 ml of HBBS in a beaker. The membrane surrounding the liver was ripped open with a pair of scissors to make the liver cells free. Thereafter, they were filtered through a sheet of lens paper. The filtrate thus obtained was centrifuged at 50 g for 2 min. The supernatant was removed out, followed by the centrifugation with a culture medium at the same condition, to give a suspension of liver cells. This suspension was transferred at a concentration of $5 \times 10^5$ cells/ml in a collagen-coated culture dish. The culture medium used was a Waymouth's MB 752/1 medium containing 10% fetal calf serum, 2.0 mg/ml bovine serum albumin (fraction V), $10^{-6}$ M dexamethasone, $10^{-7}$ M insulin, $5.32 \times 10^{-2}$ M L-serine, $4.07 \times 10^{-2}$ M $NaHCO_3$, 100 IU/ml penicillin, 100 µg/ml streptomycin and 5 µg/ml amphotericin B. The cells were cultured at 37° C. in an incubator with a constant humidity while supplying a mix of air (95%) and $CO_2$ (5%).

C) Test Method

After liver cells were cultured for 24 hours, the culture medium was changed by a fresh medium containing 10 mM carbon tetrachloride and a further culture for 1.5 hours allowed the carbon tetrachloride to induce a toxicity in them. Galactosamine also could induce a toxicity in liver cells by changing a fresh medium containing 1.5 mM galactosamine for a medium in which the liver cells had been cultured for 1.5 hours and culturing them for 14 hours.

Glutamic pyruvate transaminase (GPT) and sorbitol dehydrogenase (SDH) in the culture media were measured by the Reitman-Frankel method and a little modified Gerlach method.

The activity of glutathione-S-transferase was represented by the amount of the product produced by 1 mg of the protein per minute, which was measured by mixing a post mitochondrial supernatant in a test tube containing glutathione, 1-chloro-2,4-dinitrobenzene and potassium phosphate buffer and immediately measuring a vertically ascendent absorbance at 340 nm for 5 min.

The post mitochondrial supernatant was obtained by culturing liver cells, removing the medium, adding 3 ml of a 66 mM Tris-HC buffer (pH 7.4) to give a suspension of cells, subjecting the suspension to homogenization for 15 sec, and centrifuging the suspension at 12500 g for 15 min.

A modified McCord-Frivich method was used to measure the activity of superoxide dismutase (SOD) in liver cells. 100 µl of the pose mitochondrial supernatant was added with 200 µl of reagent A, 500 µl of deionized water, and 200 µl of reagent B, and allowed to stand at 37° C. for 30 min. After the resulting supernatant was again added with 200 µl of reagent C and allowed to stand at room temperature for 20 min, the absorbance at 550 nm was measured to calculate SOD unit.

For the activity of GSSG reductase, 200 µl of the post mitochondrial supernatant was added in a test tube containing 600 µl of a phosphate buffer, 100 µl of 10 mM GSSG and 100 µl of 1 mM NADPH and the change in the absorbance at 340 nm for 2 min was detected.

For the measurement of the total content of glutathione (GSH and GSSG), 700 µl of 0.3 mM NADPH and 100 µl of 6 mM DTNB were added to 200 µl of the pose mitochondrial supernatant which was, then, incubated at 30° C. in a water bath. After the initiation of reaction by adding 10 µl of GSH reductase (50 units/ml), the change in the absorbance at 412 nm was detected every 15 sec for 2 min.

As for the content of glutathione (oxidized form, GSSG), a mixture of 2 µl of 2-vinylpridine per 100 µl of the post mitochondrial supernatant was vigorously stirred and allowed to stand at 25° C. for 60 min to produce a GSH derivative whose content was, then, measured for the calculation of the residual GSSG.

To detect RNA biosynthesis, [$^3$H]-uridine was added to a concentration of 1 µCi/ml of culture medium and the incorporation of the radio-labeled uridine into the RNA of culture cells was measured. For this, after the culture medium was removed, the cells were washed three times with HBSS and added with 1 ml of 10% trichloroacetic acid to precipitate proteins. 1 ml of a mix of ethanol-ether (3:1) was added to remove residual trichloroacetic acid and the proteins were dissolved in 200 µl of 1N NaOH. 100 µl of the protein solution was taken and added to 3 ml of aquasol, a scintillation cocktail for the measurement of radioactivity.

D) Results

WS-TECA was administered to primarily cultured liver cells of the wistar which had been toxicity-induced by carbon tetrachloride, at an amount ranging from 1 µg/ml up to 300 µ/ml. Showing a dose-dependent effect from 1 µg/ml up to 100 µg/ml, WS-TECA reduced the activity of GPT and SDH released into culture medium with a maximal protection activity of liver cell being showed at 100 µg/ml. In addition, WS-TECA increased the activities of GSSG reductase and SOD, which played a role in hindering the production of the GST free radicals taking part in the detoxicatlon of various enzymes in the liver and in removing the free radicals produced. Whereas, WS-IECA increased the amount of GSH reduced owing to the free radicals. As mentioned above, WS-TECA exhibited a maximal activity of 50–60% at 100 µg/ml (see Table 1).

When the primarily cultured liver cells of wistar which had been led to toxicity by galactosamine, was treated with an amount of 1 µg/ml up to 300 µg/ml of WS-TECA, the activities of GPT and SDH were maximally inhibited at 300 µg/ml.

As for the influence of WS-TECA upon the RNA synthesis in the liver cells damaged by galactosamine, the liver cells were increased in RNA biosynthesis twice upon the addition of 300 µg/ml of WS-TECA as much as upon the addition of no WS-TECA and thus, up to 40% of the damaged liver cells were restored to the normal state.

TABLE 1

Effect of WS-TECA on Liver Cell Toxicity induced by $CCl_4$

| Condition | Protection (%)* | | | | | |
|---|---|---|---|---|---|---|
| | GPT | SDH | GST | GSH | GSSG | SOD |
| Control** | 100 | 100 | 100 | 100 | 100 | 100 |
| Reference*** | 0 | 0 | 0 | 0 | 0 | 0 |
| WS-TECA 1 µg/ml | 10.1 | 3.0 | 2.8 | 6.6 | 13.9 | 15.8 |
| WS-TECA 10 µg/ml | 26.9 | 14.9 | 5.4 | 12.7 | 55.8 | 31.6 |
| WS-TECA 50 µg/ml | 35.2 | 34.3 | 36.8 | 26.1 | 60.0 | 36.8 |
| WS-TECA 100 µg/ml | 64.5 | 55.8 | 49.2 | 57.0 | 63.9 | 57.9 |
| WS-TECA 300 µg/ml | 53.6 | 41.7 | 38.0 | 45.5 | 55.8 | 47.4 |

*Protection (%) = (Reference-Sample)/(Reference-Control)
**control: untreated liver cells
***reference: $CCl_4$-treated liver cells

TABLE 2

Effect of WS-TECA on Liver Cell Toxicity induced by $CCl_4$

| Condition | Protection (%)* | | RNA synthesis (cpm) |
|---|---|---|---|
| | GPT | SDH | |
| Control** | 100 | 100 | 615 ± 48 |
| Reference*** | 0 | 0 | 125 ± 11 |
| WS-TECA 1 µg/ml | 10.8 | 12.2 | 109 ± 32 |

TABLE 2-continued

Effect of WS-TECA on Liver Cell Toxicity induced by $CCl_4$

| Condition | Protection (%)* | | RNA synthesis (cpm) |
|---|---|---|---|
| | GPT | SDH | |
| WS-TECA 10 μg/ml | 18.5 | 19.1 | 204 ± 29 |
| WS-TECA 100 μg/ml | 30.8 | 32.7 | 234 ± 14 |
| WS-TECA 300 μg/ml | 41.5 | 43.9 | 267 ± 58 |

*Protection (%) = (Reference-Sample)/(Reference-Control)
**control: untreated liver cells
***reference: galactosamine-treated liver cells

E) Anti-Fibrosis Effect

A test animal was induced to be of liver fibrosis by a bile-duct ligation technique or by the treatment of carbon tetrachloride. WS-TECA obtained in the present invention was administered to a test animal to quantitatively evaluate serum procollagen N-terminal peptide (PIIIP) and hydroxyproline, thus measuring the collagen biosynthesis and accumulation in tissue, a main factor causing the fibrosis process.

Test procedures and the anti-fibrosis of WS-TECA were as follows.

The bile duct ligation method was carried out in such a way that the abdomen of a male SD rat (200–220 g) was cut open and the bile duct was subjected to double ligation for 4 weeks to induce the fibrosis of liver cells. A drug was peritoneally administered once a day. Using a rabbit anti-PIIIP antibody, the PIIIP in serum was quantitatively measured by an ELISA method. The quantitation of the collagen in the liver tissue was performed by a coloring method in which the hydroxyproline released when the liver tissue was acid-hydrolyzed was treated with chloramine T and ER solution (p-dimethylaminobenzaldehyde, perchloric acid, isopropanol).

As for the anti-fibrosis effect in the bile duct ligation test, WS-TECA could decrease the hydroxyproline amount, an index of liver fibrosis (see Table 3). In addition, the PIIIP concentration in serum, used as an index of collagen biosynthesis, could be inhibited by WS-TECA (see Table 4). As apparent from these facts, WS-TECA was effective for relieving the fibrosis of liver.

Following is a test of the liver fibrosis induced by carbon tetrachloride.

$CCl_4$ was peritoneally administered to a male SD rat at a dose of 480 mg per weight twice a week for 4 weeks. The test drug dissolved in a physiological saline was also peritoneally administered once a day for 4 weeks. The PIIIP in serum and the collagen in liver tissue were quantitated in the same manner with that of the bile duct ligation test.

The $CCl_4$ treatment resulted in a more relieved fibrosis induction than does the bile duct ligation and the liver tissue treated with $CCl_4$ made collagen deposited in itself twice as much as a control, which is treated with no drugs.

Showing a dose-dependent effect, WS-TECA inhibited the deposition of collagen in liver tissue (see Table 5) as well as lowered the concentration of PIIIP in serum (see Table 6).

These data demonstrated that WS-TECA might be useful to relieve the liver fibrosis, attributed to the increase of collagen synthesis and the deposition of collagen in liver tissue, by hindering the synthesis of collagen.

TABLE 3

Inhibitory Effect of WS-TECA on Deposition of Hydroxyproline in Liver Tissue

| Group | Total hydroxyproline in Liver Tissue |
|---|---|
| Control | 32.11 ± 6.07 |
| Bile duct-ligated | 162.2 ± 127 |
| WS-TECA administered | |
| 1.5 mg/kg | 111.2 ± 60.6 |
| 5.0 mg/kg | 96.4 ± 51.7 |

TABLE 4

Lowering Effect of WS-TECA on Concentration of PIIIP Serum

| Group | PIIIP Conc. in Serum |
|---|---|
| Control | 6.1 ± 2.9 |
| Bile duct-ligated | 37.4 ± 12.9 |
| WS-TECA administered | |
| 1.5 mg/kg | 25.5 ± 6.4 |

TABLE 5

Inhibitory Effect of WS-TECA on Deposition of Collagen in $CCl_4$-treated Rat

| Group | Total hydroxyproline in Liver Tissue |
|---|---|
| Control | 1.67 ± 0.26 |
| $CCl_4$-treated | 3.02 ± 0.78 |
| WS-TECA administered | |
| 0.5 mg/kg | 3.29 ± 1.34 |
| 1.5 mg/kg | 2.39 ± 0.89 |
| 5.0 mg/kg | 2.18 ± 1.03 |

TABLE 6

Lowering Effect of WS-TECA on PIIIP Concentration in Serum in $CCl_4$-treated Rat

| Group | PIIIP Conc. in Serum |
|---|---|
| Control | 7.4 ± 2.9 |
| Bile duct-ligated | 47.2 ± 7.8 |
| WS-TECA administered | |
| 0.5 mg/kg | 32.8 ± 9.2 |
| 1.5 mg/kg | 26.1 ± 3.5 |
| 5.0 mg/kg | 27.6 ± 6.3 |

A better understanding of the present invention may be obtained through the following examples which are set forth to illustrate, but are not to be construed as the limit of the present invention.

EXAMPLE I

To 4.7 kg of dried *Centella asiatica* was added 32 liters of 70% ethanol which was, then, subjected to cold-precipitation for 48 hours. The resulting extract in ethanol was placed in a bottle, added with 17 liters of methylene chloride and stirred for 1 hour. After complete phase separation, the upper layer was taken, added with 5 liters of ethanol and 7 liters of methylene chloride, and stirred for 1 hour. Again, after complete phase separation, the upper layer was taken and extracted by use of 17 liters of normal butanol. The extract in the normal butanol layer was washed several times with a 0.1 N NaOH solution and then, several times with water. The butanol layer was concentrated in vacuo to one tenth in volume and the resulting concentrate was mixed with 5 liters of ethyl acetate for crystallization. The crystal thus obtained was filtered with suction to obtain a solid residue. Subsequently, it was washed with a little amount of ethyl acetate, dried in vacuo at 50° C. for 24 hours, to yield 120 g of a yellowish solid.

EXAMPLE II

To 5 kg of *Centella asiatica* was added 35 liters of 70% ethanol which was, then, allowed to stand at 10° C. for 48 hours.

The extract in ethanol thus obtained was placed in a bottle and treated in the same manner with that of Example I, to yield 125 g of a mix of asiaticoside and madecassoside (4:6).

EXAMPLE III

A mix extract of asiaticoside and madecassoside (6:4) was obtained in the same manner with that of Example I.

EXAMPLE IV

A silica gel (70–230 mesh) was filled in a column with a diameter of 6 cm and a length of 26 cm by using a mobile phase (normal butanol:ethanol:ammonia water:water=60:40:5:10). Thereafter, 1 g of WS-TECA was dissolved in as little amount of the mobile phase as possible and loaded thereon. The mobile phase was allowed to flow at a constant rate and fractionated in 25 ml bottles to obtain 400 mg of pure asiaticoside and madecassoside each.

TEST EXAMPLE 5 g of WS-TECA was dissolved in 100 ml of methanol which was, then, added with 3 ml of 5N NaOH and heated for 12 hours with reflux. The resulting solution and a conventional TECA were developed on a stationary phase with a mobile phase (normal butanol:ethanol:ammonia water=60:40:5:10) and colored by a mix of anhydrous acetic acid and sulfuric acid (9:1), to identify the hydrolysates of WS-TECA with madecassic acid and asiatic acid.

The HPLC analysis of the hydrolysates showed that asiaticoside and madecassoside were present at a ratio of 5:5.

In many countries, chronic liver diseases, such as viral hepatitis and alcoholic hepatitis, occur very frequently every year, recording a high death rate. Such liver diseases continuously bring injury into the liver cells which are, thus, led to liver fibrosis. Up to now, colchichine and UDCA have been tried for treating the liver diseases but there are many different views concerning their effect. Therefore, it is pressing to develop a novel therapeutic agent capable of reducing the damage and fibrosis of liver cells. As described above, the mix of asiaticoside and madecassoside, extracted from *Centella asiatica*, is expected to be able to reduce the serosity of the chronic liver diseases as well as the death rate owing to the diseases.

The present invention has been described in an illustrative manner, and it is to be understood the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. A method for isolating a water-soluble extract of asiaticoside and madecassoside from *Centella asiatica*, comprising:

subjecting an aqueous alcohol containing *Centella asiatica* to cold-precipitation to obtain an extract;

treating the extract in the aqueous alcohol with a halogenide solvent for layer separation;

extracting the aqueous layer with a higher alcohol;

washing the extract in the alcohol layer with sodium hydroxide and then with water;

concentrating the extract;

crystallizing the extract with ethyl acetate to obtain crystals; and washing the crystals.

2. The method of claim 1, wherein said aqueous alcohol is an ethanol or methanol solution, said halogenide solvent is selected from the group consisting of methylene chloride, chloroform, and dichloroethane, and said higher alcohol is selected from the group consisting of normal butanol, sec-butanol, and amyl alcohol.

* * * * *